United States Patent
Goebel et al.

(10) Patent No.: US 10,031,082 B2
(45) Date of Patent: Jul. 24, 2018

(54) COMPOSITIONAL ANALYSIS OF A GAS OR GAS STREAM IN A CHEMICAL REACTOR AND METHOD FOR PREPARING CHLOROSILANES IN A FLUIDIZED BED REACTOR

(71) Applicant: Wacker Chemie AG, Munich (DE)

(72) Inventors: Thorsten Goebel, Emmerting (DE); Walter Haeckl, Zeilarn (DE); Wolfgang Muenzer, Kirchdorf (DE); Uwe Paetzold, Burghausen (DE); Natalia Sofina, Burghausen (DE)

(73) Assignee: WACKER CHEMIE AG, Munich (DE)

( * ) Notice: Subject to any disclaimer, the term of this patent is extended or adjusted under 35 U.S.C. 154(b) by 231 days.

(21) Appl. No.: 14/899,147

(22) PCT Filed: Jun. 17, 2014

(86) PCT No.: PCT/EP2014/062676
§ 371 (c)(1),
(2) Date: Dec. 17, 2015

(87) PCT Pub. No.: WO2015/000696
PCT Pub. Date: Jan. 8, 2015

(65) Prior Publication Data
US 2016/0131584 A1    May 12, 2016

(30) Foreign Application Priority Data
Jul. 2, 2013   (DE) .................. 10 2013 212 908

(51) Int. Cl.
*G01N 21/65* (2006.01)
*C01B 33/107* (2006.01)
(Continued)

(52) U.S. Cl.
CPC .......... *G01N 21/65* (2013.01); *B01D 53/685* (2013.01); *C01B 33/10742* (2013.01);
(Continued)

(58) Field of Classification Search
CPC ...... C01F 7/62; C01F 7/22; C01F 5/30; C01P 2006/80; C22B 21/0046; C01G 49/10;
(Continued)

(56) References Cited

U.S. PATENT DOCUMENTS

| 4,044,109 A | 8/1977 | Kotzsch et al. |
| 4,092,446 A | 5/1978 | Padovani et al. |

(Continued)

FOREIGN PATENT DOCUMENTS

| CN | 1934119 A | 3/2007 |
| DE | 10 2004 014 220 A1 | 10/2005 |

(Continued)

*Primary Examiner* — Jennifer Wecker
(74) *Attorney, Agent, or Firm* — Brooks Kushman P.C.

(57) ABSTRACT

The composition of a gas or gas stream containing $AlCl_3$ in a chemical reactor is measured by removing $AlCl_3$ from the gas and analyzing the gas by gas chromatography or spectroscopy. Chlorosilanes may be prepared in a fluidized bed reactor having a reactor height H0, in which supplied HCl reacts with silicon, wherein a temperature profile in the fluidized bed reactor is greater than $S1(H/H0)=(a1-b1)*(1/(1+\exp(-c1((H/H0)-d1))))+b1$ and less than $S2(H/H0)=(a2-b2)*(1/(1+\exp(-c2((H/H0)-d2))))+b2$, where $a1=100°$ C., $a2=300°$ C., $b1=300°$ C., $b2=400°$ C., $c1=50$, $c2=20$, $d1=0.2$, and $d2=0.8$.

14 Claims, 6 Drawing Sheets (51) Int. Cl.
*G01N 21/3504* (2014.01)
*G01N 30/14* (2006.01)
*G01N 30/86* (2006.01)
*B01D 53/68* (2006.01)

(52) U.S. Cl.
CPC ... *C01B 33/10763* (2013.01); *G01N 21/3504* (2013.01); *G01N 30/14* (2013.01); *G01N 30/86* (2013.01); *B01D 2251/304* (2013.01); *B01D 2251/60* (2013.01); *B01D 2253/112* (2013.01); *B01D 2257/204* (2013.01); *B01D 2257/2045* (2013.01); *B01D 2258/02* (2013.01); *G01N 2201/06113* (2013.01); *G01N 2201/08* (2013.01)

(58) Field of Classification Search
CPC ...... C01G 23/0475; C01G 31/04; C01B 9/02; C01B 33/08; C01B 33/1071; C01B 33/10763; C01B 33/10742; B01D 7/02; B01D 37/00; B01D 53/685; B01D 2253/112; B01D 2251/304; B01D 2251/60; B01D 2257/204; B01D 2257/2045; B01D 2258/02; G01N 21/3504; G01N 21/65; G01N 30/14; G01N 30/86; G01N 2201/06113; G01N 2201/08
See application file for complete search history.

(56) References Cited

U.S. PATENT DOCUMENTS

| | | | |
|---|---|---|---|
| 4,125,586 A * | 11/1978 | Glaeser | C01G 23/024 423/122 |
| 5,871,705 A | 2/1999 | Sakata et al. | |
| 7,368,590 B2 | 5/2008 | Kalchauer et al. | |
| 9,765,271 B2 * | 9/2017 | Myrick | C06B 45/30 |
| 2007/0193696 A1* | 8/2007 | Kalchauer | C01F 11/24 159/48.1 |
| 2009/0016947 A1 | 1/2009 | Fabry et al. | |
| 2009/0060818 A1 | 3/2009 | Bill, Jr. et al. | |
| 2010/0264362 A1* | 10/2010 | Chee | B01J 8/0055 252/182.1 |
| 2011/0059004 A1 | 3/2011 | Stoecklinger | |
| 2011/0297884 A1 | 12/2011 | Chee et al. | |
| 2012/0189526 A1 | 7/2012 | Petrik et al. | |

FOREIGN PATENT DOCUMENTS

| | | |
|---|---|---|
| DE | 10 2006 009 954 A1 | 9/2007 |
| EP | 2 243 745 A2 | 10/2010 |
| WO | 00/39078 A1 | 7/2000 |
| WO | 02/44186 A1 | 6/2002 |
| WO | 2006031120 A1 | 3/2006 |
| WO | 2010/135105 A1 | 11/2010 |
| WO | 2011026670 A2 | 3/2011 |

* cited by examiner

COMPOSITIONAL ANALYSIS OF A GAS OR GAS STREAM IN A CHEMICAL REACTOR AND METHOD FOR PREPARING CHLOROSILANES IN A FLUIDIZED BED REACTOR

CROSS REFERENCE TO RELATED APPLICATIONS

This application is the U.S. National Phase of PCT Appln. No. PCT/EP2014/062676 filed Jun. 17, 2014, which claims priority to German Application No. 10 2013 212 908.4 filed Jul. 2, 2013, the disclosures of which are incorporated in their entirety by reference herein.

BACKGROUND OF THE INVENTION

1. Field of the Invention

The subject matter of the invention pertains to a method for analyzing the composition of a gas or gas stream in a chemical reactor. The invention pertains more particularly to the application of such a method to gases or gas streams which arise during the production of chlorosilanes and organochlorosilanes, and to a method for preparing chlorosilanes in a fluidized bed reactor.

2. Description of the Related Art

The preparation of trichlorosilane (TCS) is accomplished by reaction of metallurgical silicon (mg-Si) with HCl or by reaction of mg-Si with silicon tetrachloride (STC) and hydrogen and/or HCl. Methylchlorosilanes are prepared by reaction of mg-Si with methylchloride.

U.S. Pat. No. 4,092,446 A discloses a reactor in which a stream of hydrogen chloride is passed through a silicon bed consisting of silicon particles. The hydrogen chloride reacts with the silicon particles to form silicon tetrachloride (STC) and TCS and hydrogen.

For the economic optimization of chlorosilane syntheses in terms of the yields of the respective target products, the analysis of the gaseous reaction products is of great importance.

For example, the reaction of mg-Si with HCl leads to a product spectrum encompassing the principle product TCS (>80%), byproducts such as STC (<20%) and dichlorosilane (DCS) (<2%), plus various trace impurities. Moreover, the reaction gas also comprises $H_2$ and unreacted HCl.

The objective of the TCS synthesis is usually for a maximum TCS yield in conjunction with complete or near-complete HCl conversion, since recovery of the HCl from the reaction offgas leads to additional costs.

US 2012189526 A1 discloses a method for preparing trichlorosilane by reacting silicon particles with tetrachlorosilane and hydrogen, and optionally with hydrogen chloride, in a fluidized bed reactor to give a trichlorosilane-containing product gas stream, the fluidized bed reactor having at least one inlet for tetrachlorosilane and hydrogen and also, optionally, for hydrogen chloride, at least one inlet for the silicon particles which form a fluidized bed with the tetrachlorosilane and hydrogen, and at least one outlet for the trichlorosilane-containing product gas stream, this outlet being preceded by at least one particle separator which selectively allows the passage only of silicon particles up to a certain maximum particle size, the characteristic feature being that silicon particles are discharged from the reactor via at least one further outlet without such a particle separator, continuously or at regular time intervals.

US 20110297884 A1 describes how a plurality of temperature measurement points positioned horizontally and vertically in the reactor are suitable for monitoring the time profile of the temperature changes in the reactor.

The reactor, however, is controlled using only one of these temperature measurement points, which lies at the upper end of the fluidized bed.

Within defined limits, a particular temperature is considered advantageous as a control variable under the selected operating conditions.

A variety of methods are described in the literature for increasing the TCS yield.

Besides compliance with particular reaction conditions, such as the quenching of the reaction gas, for example, catalysts are frequently employed in these methods. An increase in the HCl conversion is achievable, for example, through an increase in the temperature and the addition of catalysts.

A problem here is that measures for increasing the HCl conversion frequently entail a reduction in the TCS selectivity (e.g., temperature rise), or vice versa (quench, improved cooling).

In practice, therefore, it is difficult at the same time to bring about the optimum reaction conditions for TCS selectivity and for HCl conversion.

Even optimum operating conditions, once set, undergo change over the course of the reaction time. In the course of continuously operated TCS synthesis, the reactor accumulates impurities and also, possibly, catalytically active constituents, which adversely affect both TCS selectivity and HCl conversion.

It is therefore necessary to remove these impurities from the reactor regularly. This as well induces fluctuations in the TCS selectivity and in the HCl conversion.

In the reaction of metallurgical silicon (mg-Si) and HCl to give TCS ($HSiCl_3$), hydrogen and byproducts are formed:

$$Si+3\ HCl=HSiCl_3+H_2+\text{byproducts} \qquad (1)$$

The amount of the byproducts formed in the reaction (1) and hence the TCS selectivity, defined as mole fraction TCS/(TCS+byproducts), is influenced by a number of factors, including the catalytic effect of impurities (accompanying elements) in the mg-Si used.

It is known that impurities in mg-Si or addition of a catalyst to mg-Si may influence the selectivity of the reaction. Certain impurities have a positive influence, hence raising the selectivity. Other impurities, in contrast, have a negative influence.

US 20090060818 A1 claims a method for preparing TCS by reaction of silicon with HCl, or STC with hydrogen in the presence of silicon and catalysts. Examples of the catalyst used are Fe, Cu, Al, V, Sb or compounds thereof. Silicon and catalysts are laminated with one another and comminuted prior to the reaction. The effects of direct contact between silicon and catalyst include a distinct reduction in the yield of byproducts, thereby increasing the TCS selectivity.

U.S. Pat. No. 5,871,705 A proposes a method for preparing TCS by reaction of silicon with hydrogen chloride, comprising the contacting of at least one silane compound selected from the group consisting of dichlorosilane (DCS), monochlorosilane (MCS) and monosilane, with silicon, during or before the reaction between silicon and hydrogen chloride. Silicon is therefore contacted with a silane compound in order to remove the oxide layer on the silicon surface and hence to raise the reactivity toward HCl. Also disclosed is the conduct of the reaction between the silicon and hydrogen chloride in the presence of a catalyst with catalytic activity for the preparation of TCS from silicon and hydrogen chloride, and of an alkali metal compound. This suppresses the reaction to give STC, and therefore raises the TCS selectivity.

WO 2006031120 A1 describes a method for preparing TCS by reaction of Si with HCl gas at a temperature between 250 and 1100° C. and a pressure of 0.1-30 atm in a fluidized bed reactor, in an agitated bed reactor, or in a fixed bed reactor, wherein the Si supplied to the reactor contains less than 100 ppm of Mn. The use of mg-Si with more than 100 ppm of Mn or addition of Mn to the reactor leads to lower reactivity and TCS selectivity.

For determining the yields of the TCS synthesis, the usual approach to date has been to condense and then analyze the chlorosilanes present in the reactor offgas. This type of offline analysis, e.g., offline gas chromatography (GC), takes up a fair amount of time and is prone to error on account of the differences in condensability of the sample constituents. With this methodology, moreover, it is not possible to determine the fractions of $H_2$, $N_2$ and HCl.

WO 2010135105 A1 discloses a method for analyzing gases in a method for preparing high-purity silicon, in which a gas or gas mixture comprising one or more of the gases in the $H_2$, $SiH_4$, $H_3SiCl$, $HSiCl_3$, $H_2SiCl_2$, HCl, $SiCl_4$ and $N_2$ group is exposed to the radiation of a Raman spectrometer in order to give a Raman signal for each of the gases present and to analyze these signals in order to ascertain the presence and concentration of any one of the gases present. The possibility for simultaneous measurement of chlorosilanes, and also $H_2$, $N_2$ and HCl, by means of Raman spectroscopy is viewed as an advantage for rapid intervention in the processes for the deposition of polysilicon and for the conversion of STC to TCS.

WO 2011026670 A2 discloses a method for controlling a plant for the preparation of polycrystalline silicon, in which the plant comprises at least one reactor having at least one feed line and one offtake line for a gas mixture, the method characterized by the following steps:

samples for measurement are taken from the feed line and the offtake line of each reactor;
  the samples for measurement that are taken are supplied, each via a line, to at least one gas chromatograph;
  measurement values obtained using the gas chromatograph and relating to the composition of the measurement samples supplied are used to derive control signals; and
  the control signals obtained, by means of a controlling and regulating unit, are used to adjust, via actuating elements, a multiplicity of parameters of the at least one reactor in such a way that the efficiency of the plant is guided automatically to a production optimum.

It has emerged that the methods described in WO 2010135105 A1 and in WO 2011026670 A2 are disadvantageous when used to analyze gas streams from silane syntheses. It has been observed that particles are deposited on the measuring cells or on optical components. Cleaning the measuring equipment has not been able to provide a remedy, since the particles are evidently abrasive particles which may damage the components.

It has also been ascertained that there are alterations in the background of the spectra and there is a continuous loss in intensity of the signals, and that these factors make analytical evaluation more difficult or else impossible. In the case of gas chromatography, there were instances of blocking in lines and valves, and also of unwanted reactions with the separation medium in the column of the gas chromatograph.

The problems which have been observed in the prior art, such as depositions on or damage to components, losses in intensity of the spectra, instances of blocking or reaction with separation medium, do not occur in the method of the invention. The inventors assume that the problems in the prior art are caused by depositions of $AlCl_3$ and/or dust particles. The resublimation of $AlCl_3$ on colder points of the measuring apparatus (e.g., of the optical components) would appear to lead to a continuous loss of intensity of the signals and to further alterations in the Raman spectrum, which would no longer permit reliable evaluation.

The problems described gave rise to the objective of the invention.

SUMMARY OF THE INVENTION

The invention is directed to a method for analyzing the composition of a gas or gas stream comprising $AlCl_3$ in a chemical reactor, comprising the removal of $AlCl_3$ from the gas and the subsequent analysis of the gas by means of gas chromatography or spectroscopy.

The invention is also directed to a method for preparing chlorosilanes in a fluidized bed reactor having a reactor height H0, in which supplied HCl reacts with silicon, characterized in that a temperature profile in the fluidized bed reactor is greater than $S1(H/H0)=(a1-b1)*(1/(1+\exp(-c1((H/H0)-d1))))+b1$ and less than $S2(H/H0)=(a2-b2)*(1/(1+\exp(-c2((H/H0)-d2))))+b2$, where a1=100° C., a2=300° C., b1=300° C., b2=400° C., c1=50, c2=20, d1=0.2, d2=0.8.

DETAILED DESCRIPTION OF THE PREFERRED EMBODIMENTS

Such gases or gas streams comprising AlCl3 are produced in particular in the synthesis of chlorosilanes or organochlorosilanes, as for example in the preparation of trichlorosilane (TCS) by reaction of mg-Si with HCl, the reaction of mg-Si with silicon tetrachloride (STC) and hydrogen and/or HCl, and also in the synthesis of methylchlorosilanes by reaction of mg-Si with methyl chloride.

The inventors have recognized for the first time that the vertical temperature profile over the entire reactor height, in other words including the temperature profile in the gas space above the fluidized bed, is important for the operating regime, whereas the prior art (cf. US 20110297884 A1) controlled only one of a number of temperature measurement points in the reactor, namely that situated at the upper end of the fluidized bed.

The data obtained by a method for analyzing the composition of a gas or gas stream comprising $AlCl_3$, comprising removal of $AlCl_3$ from the gas and subsequent analysis of the gas by means of gas chromatography or spectroscopy, and relating to the composition of the gas or gas stream, are preferably used for establishing the temperature profile in the fluidized bed reactor.

With the stated methods for the analysis of the composition of a gas or gas stream, mg-Si is employed as a starting material. Commercially available mg-Si contains up to several 1000 ppmw of aluminum. At least part of the aluminum is consumed by reaction at a temperature of more than 300° C. with HCl and/or chlorosilanes to give $AlCl_3$. Since $AlCl_3$ sublimes at a temperature of more than 180° C., it is in gaseous form in the reaction product at the reactor outlet.

Provision is made to remove $AlCl_3$ from the gas before the composition of the gas is analyzed. The removal of the $AlCl_3$ is accomplished preferably by absorption on sodium chloride. Through formation of a double salt ($NaAlCl_4$), $AlCl_3$ is removed efficiently from the gas stream, without further alteration to the composition of the gas stream. Particulate solids in the gas stream can also be removed at the same time.

For the analysis of the gas mixture, in combination with the absorption unit for $AlCl_3$, it is possible to use the common online analytical techniques, such as GC and IR and Raman spectroscopy. Raman spectroscopy is particularly preferred for utilization in the analysis of the composition.

The data obtained from the analytical technique are used preferably for the control of reactors for preparing chlorosilanes and/or organochlorosilanes, preferably for controlling a reactor for the direct synthesis of trichlorosilane by reaction of metallurgical silicon with HCl.

The invention enables rapid and reliable determination of the composition of the reaction offgas and the alteration of reactor parameters and operating parameters in order to influence the reaction outcome.

Reactor parameters and operating parameters are preferably altered on the basis of the gas analyses in such a way as to increase the yield of the reaction product.

Reactor parameters and operating parameters are preferably altered on the basis of the gas analyses in such a way as to increase the conversion rate of a reactant.

Reactor parameters and operating parameters are preferably altered on the basis of the gas analyses in such a way that the space-time yield is optimized.

One or more reactor parameters and operating parameters are preferably altered on the basis of the gas analyses.

Particularly preferred is the specification of a form of a temperature profile and temperature ranges in the reactor on the basis of the gas analyses.

Particularly preferred is the direct coupling of one or more of the reactor parameters and operating parameters with the Raman spectrometer (online analysis with process control).

It is also preferred to combine the discharge of catalyst material with Raman measurements in such a way and to specify and/or control the time profile of the discharge on the basis of the gas analyses.

The gas analysis may yield data on selectivity, reactivity, HCl conversion, and DCS content, and allows these parameters to be influenced directly by a change in process.

Preferred embodiments of the invention are elucidated hereinafter.

Raman Spectrometer

The laser light of the spectrometer is guided to the Raman probe via an optical waveguide, and is focused after the probe.

At the focal point, inelastic Raman transitions specific to the gas under measurement are induced in the form of scattered light.

A collecting optical unit is integrated into the probe, and guides the Raman scattered light to the spectrometer via a further optical waveguide.

In the spectrometer, the Raman scattered light is imaged by a grating monochromator onto an area array camera. The Raman transitions specific to the gas under measurement are represented, in dependence on the Raman shift, as intensities in a spectrum.

The grating monochromator is configured so as to image a Raman shift of $-21$ cm$-1$ to $4417.5$ cm$-1$ in the spectrum.

A dark measurement is conducted once a day. The result obtained is a dark spectrum, which is subtracted automatically from the Raman spectrum in order to eliminate the electronic noise of the camera in the spectral data.

For each measurement, excitations of the cosmic radiation are removed from the spectral data.

The Rayleigh radiation of the laser is minimized by means of notch filters both in the probe and in the spectrometer.

The section of the probe in which the notch filter is seated is cooled.

The duration of a measuring cycle is transmitted by process software to communication software, which opens the laser shutter in the spectrometer for the mandated measuring time.

The spectral data are evaluated preferably as follows:

After one measuring cycle has elapsed, Raman transitions specific to the gas under measurement are evaluated from the Raman spectrum.

The inelastic transitions are present as intensity peaks in the spectrum.

Both the height of the peaks and the area integral are dependent on the number of the molecule-specific transition rate and the concentration of a component in the gas under measurement.

The area integral is calculated for the signals reported in Table 1.

The area integrals obtained are calibrated according to techniques familiar to one skilled in the art.

TABLE 1

| Component | Raman shift (cm−1) |
|---|---|
| TCS | 253 |
| $H_2$ | 354 |
| Sapphire | 416 |
| STC | 424 |
| TCS | 496 |
| TCS | 588 |
| Sapphire | 748 |
| TCS | 813 |
| DCS | 2248 |
| TCS | 2261 |
| $N_2$ | 2329 |
| HCl | 2884 |
| $H_2$ | 4127 |
| $H_2$ | 4145 |
| $H_2$ | 4157 |
| Sapphire | 4367 |
| Sapphire | 4397 |

As an alternative to the online analysis by means of Raman spectroscopy, an online GC with upstream salt filter has been tested successfully.

The invention is further elucidated hereinafter by FIGS. 1-6.

Figure 1:
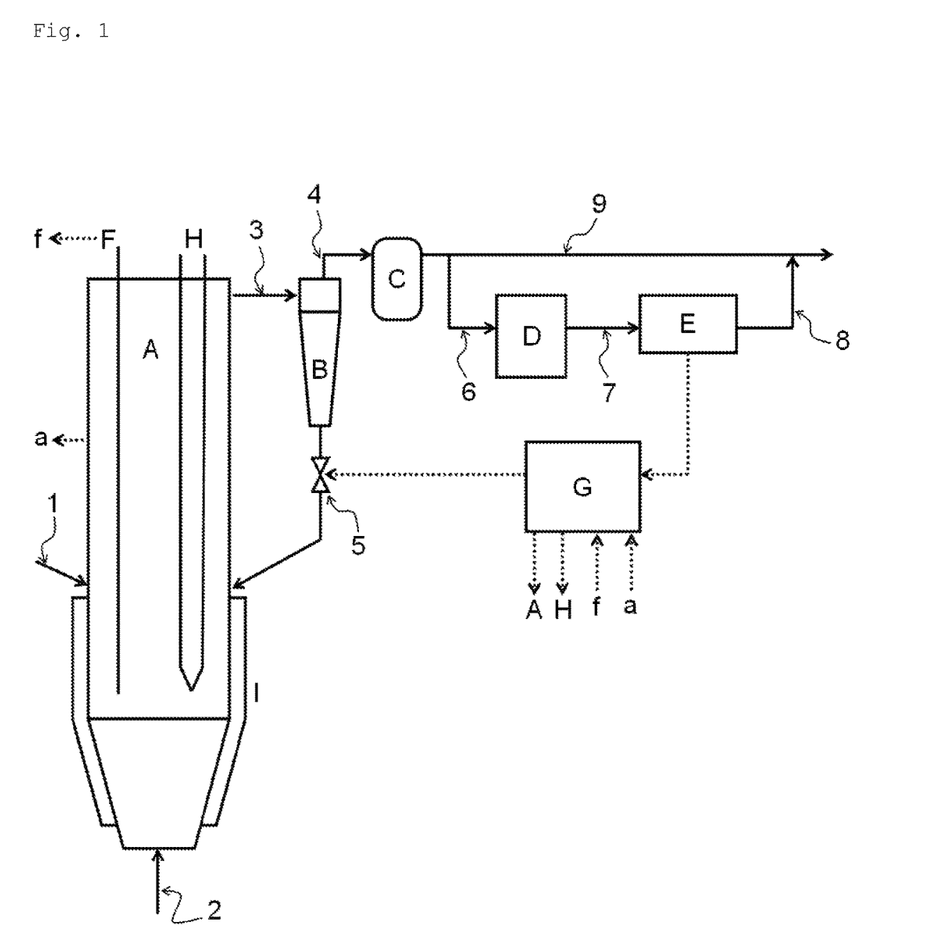
FIG. 1 shows a suitable apparatus for implementing the method.

List of Reference Symbols Used
A fluidized bed reactor
B particle separator
C particle filter
D salt filter
E measuring cell for Raman spectrometer
F thermocouple
G control unit
H cooling rods
I cooling jacket
a measuring signals from the reactor (e.g., pressures; temperatures)
f measuring signals of the thermocouple F
1 silicon supply
2 HCl supply
3 product gas line to particle separator B
4 product gas line to filter C
5 shutoff valve to interrupt the re-entry of particles from the particle separator B
6 heated bypass line to salt filter D
7 heated line to measuring cell E
8 heated return of the measuring gas into the product
9 product gas line to further treatment Process Control For the automatic monitoring of the plant it is useful to provide a withdrawal element for measurement samples in the exit line of each reactor in the plant.

For the analysis of the measuring sample taken, at least one Raman spectrometer is assigned to the plant.

FIG. 1 shows a corresponding apparatus.

The measuring sample is taken ideally at the reactor exit, preferably after the particle separator B, more preferably after further particle filters C.

The measuring sample can be supplied via a heated line 6 to the measuring unit E of the Raman spectrometer.

The measuring sample can be supplied via a heated line 6 to an interposed unit D for the removal of $AlCl_3$ from the chlorosilane-containing offgas stream.

From there, the $AlCl_3$-free offgas is supplied preferably via a heated line 7 to the measuring unit E of the Raman spectrometer.

It is economical and therefore particularly preferred for the measuring gas from the measuring cell of the Raman spectrometer to be returned to the process again at a suitable point (line 8).

It is expedient to heat the lines 6, 7 and 8 at up to 300° C. Particularly preferred are 100 to 250° C.

It is advantageous to regulate the flow rate and the pressure in line 6.

It is also useful to equip line 8 with an antibackflow device.

The measuring unit E comprises a housing with a measuring cell of the Raman spectrometer and with further particle filters.

The interior of the housing, and also the fittings located inside it, can be heated at up to 200° C. Particularly preferred are temperatures between 100 and 150° C.

The measuring cell ideally comprises a solid stainless steel block which is equipped with a dedicated heating means.

The measuring probe is accommodated in this measuring cell. The measuring gas is passed through the measuring cell. Pressure and temperature of the gas under analysis are captured in the measuring cell.

Unit D preferably comprises a container, which contains solid sodium chloride in a loose bed, and which can be heated at up to 250° C.

The $AlCl_3$-containing offgas of the reactor flows through the bed of NaCl, with the $AlCl_3$ dissolving in the NaCl and therefore being effectively removed from the offgas.

Under the temperature conditions selected, the compound formed from $AlCl_3$ and NaCl is liquid and can be collected in a collecting vessel beneath the container, and removed.

The removal is very effective, since there was no observable deposition of $AlCl_3$ in downstream systems.

Control unit G collects information and uses it to control the shutoff valve 5, the cooling performance of I, the cooling performance of H, other parameters at A, the silicon supply 1, and the metered HCl feed 2.

EXAMPLE 1

In this example, the method of the invention is contrasted with a conventional weekly analysis by means of offline GC.

The gas under measurement was analyzed with a Raman spectrometer.

A laser with a wavelength of 532 nm and a power of 150 mW was used.

Figure 2:
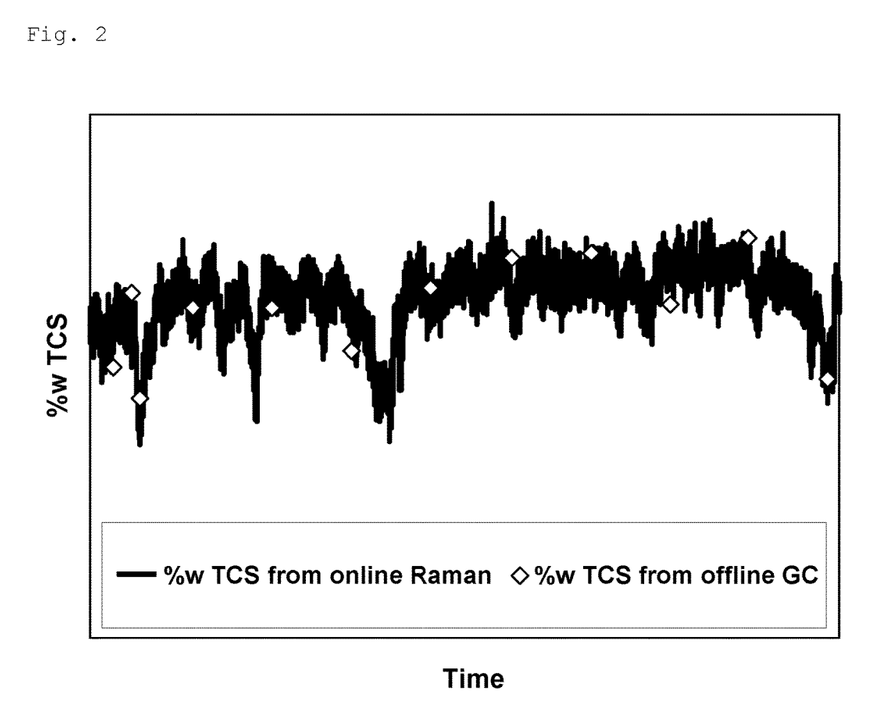
FIG. 2 shows the TCS concentration in the analyzed gas as a function of time.

FIG. 2 shows the results. The concentration of TCS in the gas under measurement was determined in each case. The advantages of the online analysis are obvious.

EXAMPLE 2

A temperature profile can be determined by means of a thermocouple installed vertically into the reactor, with temperature sensors.

Figure 3:
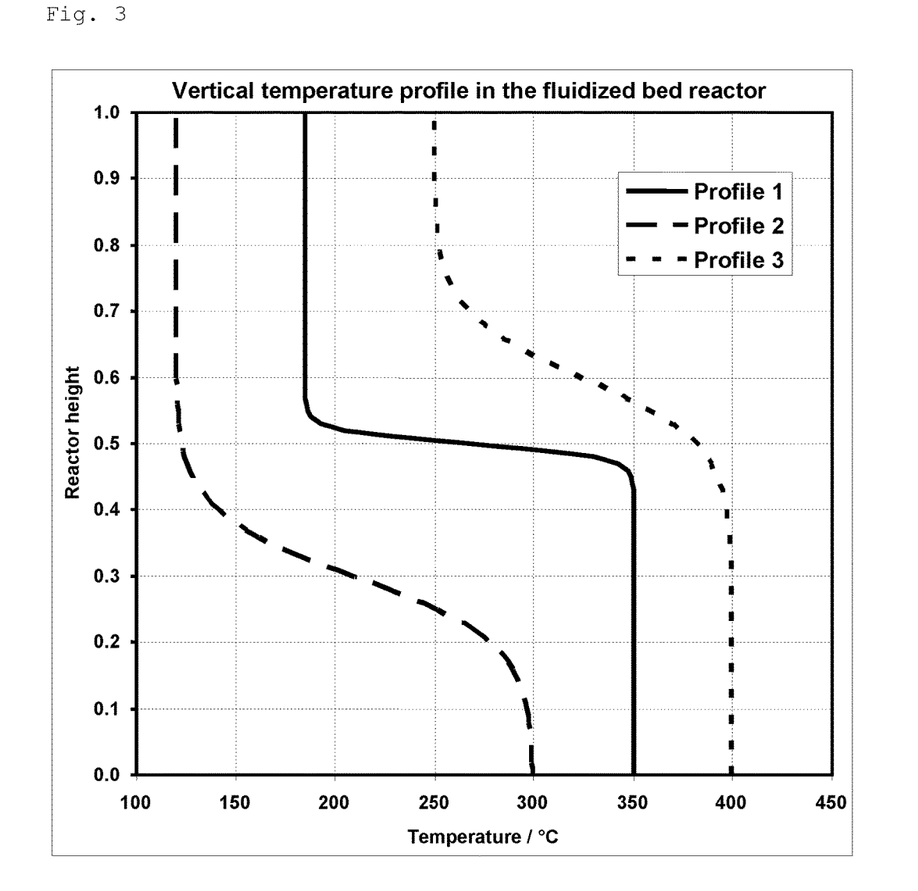
FIG. 3 shows vertical temperature profiles according to the invention in the fluidized bed reactor.

FIG. 3 shows examples of vertical temperature profiles of the invention in the fluidized bed reactor.

The reactor height (normalized) is plotted on the ordinate, the temperature on the abscissa.

A preferred form is that of an S-curve (sigmoid curve):

$$S(H/H0)=(a-b)*(1/(1+\exp(-c((H/H0)-d))))+b$$

With a reactor height normalized to one, an arbitrary temperature profile can be described unambiguously by way of four variables (Tmin, Tmax, inflection point, and slope).

a=T(min), b=T(max), c=slope, d=inflection point

Preferred ranges of a, b, c and d:

120<a<250° C., 300<b<400° C., 20<c<100, 0.2<d<0.8.

Particularly preferred ranges of a, b, c and d:

200<a<250° C., 330<b<380° C., 20<c<50, 0.3<d<0.6.

In the context of the invention, the Raman signal is utilized in order to vary the selectivity by adjustment of the temperature profile.

The temperature profile that is the most favorable in each case is dependent on other parameters and is therefore not necessarily the same for a particular selectivity.

It is necessary to take account of the fact that further parameters, such as differential pressure, amount of HCl, composition of the catalyst material, particle size distribution, or combinations of these parameters, for example, have an influence.

The composition of the catalyst material and the respective particle size distribution of a given point in time are unknown, and there is no suitable online analysis in existence for these.

An examination by means of online Raman is therefore mandatory in order to allow direct monitoring of the changes.

The effects on the temperature profile:

As described in DE 2704975 A1 it is expedient to have available not only jacket cooling but also cooling of the fluidized bed by inserted cooling lances.

The temperature profile can be adjusted by regulating jacket cooling and rod cooling, by means, for example, of adapting the quantities of coolant and/or the temperature of the cooling medium.

Preference is given to subdividing the cooling jacket into at least two zones, which can be regulated selectively.

Different lengths of cooling rods (at least two different lengths) with preferably targeted controlling of the quantities of coolant and/or of the temperature of the cooling medium are used in order to be able to selectively set temperatures at specific heights.

The temperature profile may also be influenced, furthermore, by the height of the fluidized bed.

The temperature profile can be influenced by varying the HCl supply. This relates both to the amount of HCl and to the location of the feed.

The temperature profile can be influenced by varying the flow rate in the reactor.

The temperature profile can be modified by changing the particle size/particle size distribution.

Figure 4:
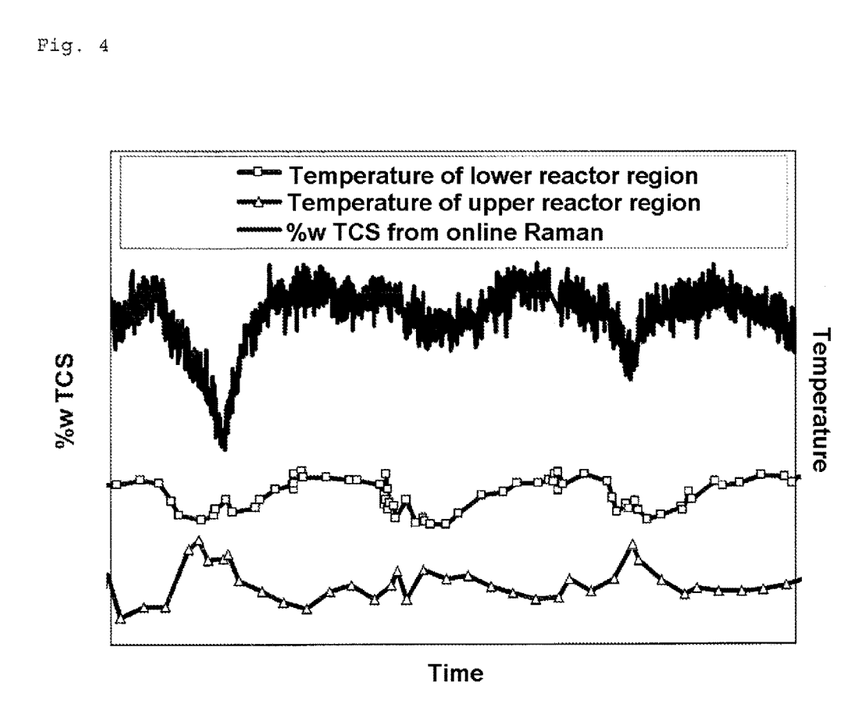
FIG. 4 shows the TCS concentration in the analyzed gas as a function of time in the case of a fluctuating temperature profile in the upper and lower regions of the reactor.

FIG. 4 shows temperature profiles at different heights in the reactor and also the TCS content from Raman data.

It is apparent from this that a change in the temperature has a direct influence on the selectivity.

The temperature is preferably regulated via the reactor height.

In this way it is possible to influence the reaction zone by the control of the temperature at different heights.

Figure 5:
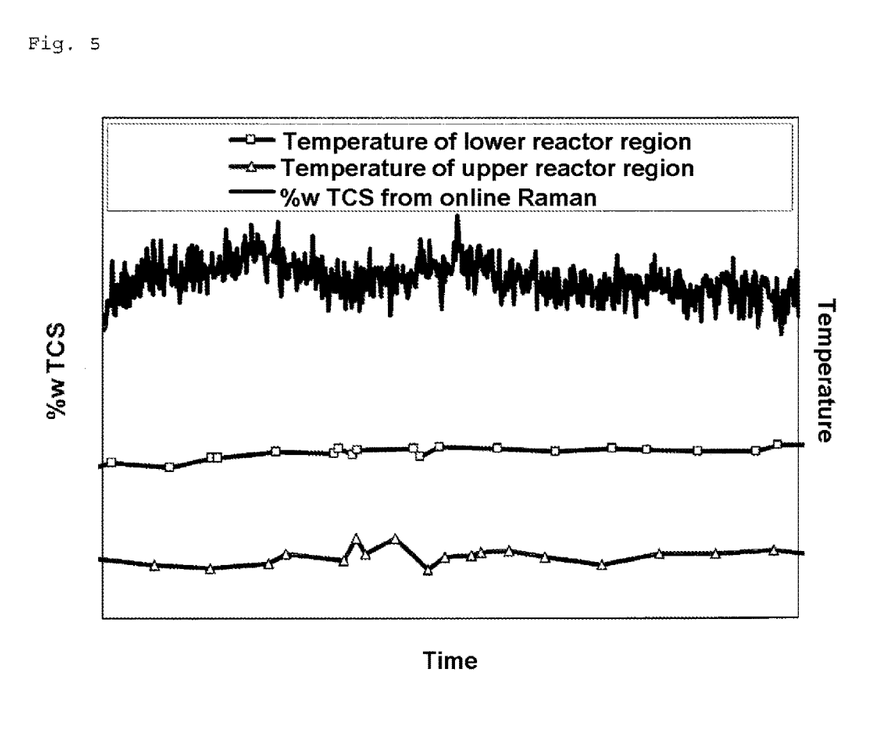
FIG. 5 shows the TCS concentration in the analyzed gas as a function of time in the case of a largely stable temperature profile in the upper and lower regions of the reactor.

FIG. 5 shows temperature profiles at different heights in the reactor and also the TCS content from Raman data.

It is clear that the stabilization of the temperature leads to stabilization of the selectivity.

EXAMPLE 3

It is known that the flow rates which prevail in the fluidized bed reactor extract particles from the fluidized bed and entrain them with the product gas stream, meaning that they are lost.

As a consequence of this, fluidized bed reactors are customarily equipped with particle separators, which pass unused material back into the reactor. The particle separators may be mounted in the reactor and also outside.

Depending on the technical configuration, the particle separators remove particles of certain sizes, to allow them to be passed back to the reactor. Smaller particles pass through the particle separator and must be removed from the product gas stream by means of filters, for example.

In the course of the reaction of metallurgical silicon with hydrogen chloride, there is an accumulation over time of heavy metals in the form of their chlorides and of relatively unreactive material in the reactor. At the same time, as a result of the chemical reaction, there is a change in the particle size distribution of the material introduced. Excessive accumulation of heavy metals and of relatively unreactive material can lead to an influence on the reactivity and the selectivity, and it is therefore undesirable from an economic standpoint. It may be necessary from time to time, therefore, to remove such material (referred to as catalyst material) from the fluidized bed reactor. Timely intervention, however, is not possible, owing to a lack of appropriate online analysis of the chemical composition of the reactor contents and of the particle size distribution.

Figure 6:
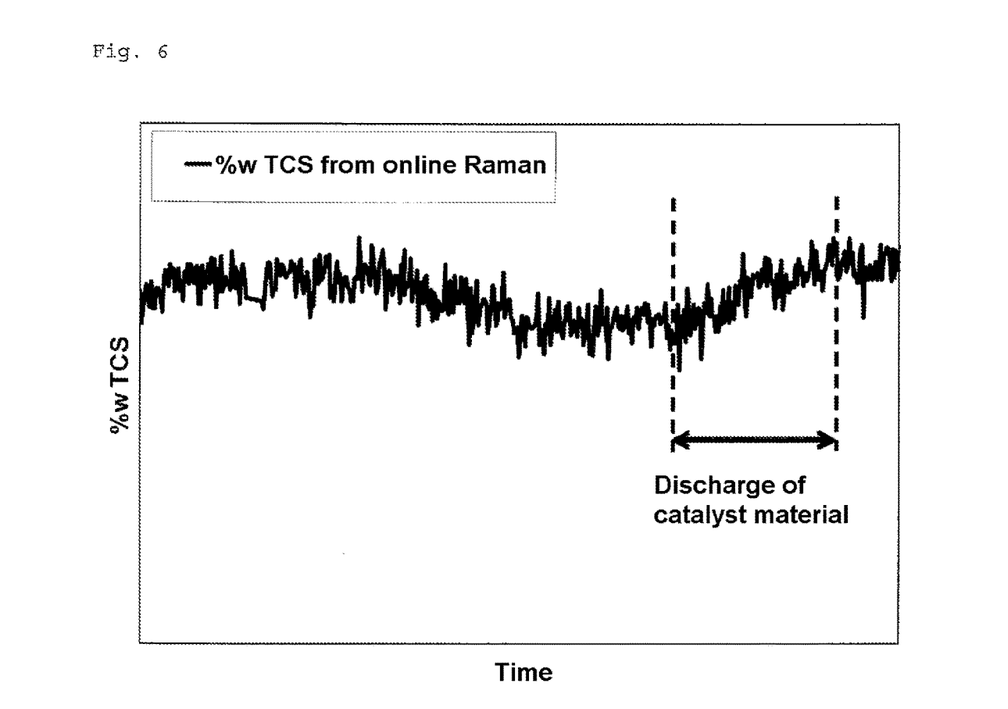
FIG. 6 shows the TCS concentration in the analyzed gas as a function of time, and the effect of a discharge of catalyst material.

FIG. 6 shows the time profile of the TCS content from Raman data. The time at which discharge of catalyst material was commenced is shown.

It is evident that the discharge of catalyst material leads to an increase in the selectivity.

The discharge may be accomplished by means, for example, of a separate outlet, as described in US 2012189526 A1, for example. A disadvantage with this technique, however, is that it makes no distinction between "good" and "bad" material, and so the material is appropriately subjected to a further workup step in order to minimize silicon losses.

Since the heavy metals form primarily as chlorides on the surface of the Si particles in the case of the chemical reaction of metallurgical silicon with HCl, these particles accumulate as a result of continual grinding processes of the silicon particles with one another, preferentially, to smaller particles, or themselves form extremely fine particles, which below a certain size are able to pass through the particle separator and hence are no longer discharged back into the reactor.

It would therefore be conceivable to optimize the particle separator to a defined particle size in such a way that the maximum possible number of highly contaminated particles leave the reactor, but at the same time the maximum amount of unconsumed material is discharged back into the reactor.

Since, however, on the industrial scale, materials employed are generally materials from different manufacturers, containing different levels of impurities, the "optimum" particle size described above may vary.

It is therefore useful to optimize the particle separator for a defined particle size fraction and, if unwanted effects occur, to increase discharge even of other particles which would normally be returned.

The online monitoring of the selectivity and the HCl slippage, for example, leads to goal-oriented and event-based discharge times and to the duration of the discharge, in order to minimize losses of "good" material.

The invention claimed is:

1. A method for analyzing the composition of a gas or gas stream comprising $AlCl_3$ exiting a fluidized bed chemical reactor having a reactor height H0 in which HCl reacts with Si forming chlorosilanes, comprising removing $AlCl_3$ from the gas or gas stream, subsequently analyzing the gas or gas stream by means of on-line gas chromatography or spectroscopy, and employing the results of analyzing the gas or gas stream to establish or modify a temperature profile in the reactor as a function of reactor height by changing at least one reactor operating parameter, wherein the temperature profile in the fluidized bed chemical reactor having a reactor height H0, is above $S1(H/H0)=(a1-b1)*(1/(1+\exp(-c1((H/H0)-d1))))+b1$ and below $S2(H/H0)=(a2-b2)*(1/(1+\exp(-c2((H/H0)-d2))))+b2$, where a1=100° C., a2=300° C., b1=300° C., b2=400° C., c1=50, c2=20, d1=0.2, and d2=0.8.

2. The method of claim 1, wherein the silicon comprises metallurgical grade silicon.

3. The method of claim 1, wherein removing $AlCl_3$, from the gas or gas stream is accomplished by absorption on solid sodium chloride.

4. The method of claim 1, further comprising removing particulate solids as well as $AlCl_3$ from the gas or gas stream.

5. The method of claim 1, wherein the gas or gas stream is analyzed by Raman spectroscopy, gas chromatography or IR spectroscopy.

6. The method of claim 1, wherein the analysis of the gas or gas stream determines at least one of the concentrations of HCl, $N_2$, $H_2$, or one or more chlorosilanes in the gas or gas stream.

7. The method of claim 1, wherein the data obtained from analysis of the gas controls the fluidized bed temperature profile of the chemical reactor.

8. The method of claim 7, wherein the reactor is a fluidized bed reactor in which trichlorosilane is prepared by reaction of metallurgical grade silicon with HCl.

9. The method of claim 8, wherein analysis of the gas is used to change one or more operating parameters so as to optimize one or more variables selected from the group consisting of chlorosilane yield, trichlorosilane selectivity, HCl conversion rate, and space-time yield.

10. The method of claim 1, wherein the analysis of the gas or gas stream is used to modify temperatures in the reactor and temperature profile as a function of a reactor height.

11. The method of claim 1, wherein analysis of the gas determines a time for discharge of catalyst material.

12. A method for preparing chlorosilanes in a fluidized bed reactor having a reactor height H0, in which HCl reacts with silicon, comprising establishing a temperature profile in the fluidized bed reactor which is above $S1(H/H0)=(a1-b1)*(1/(1+\exp(-c1((H/H0)-d1))))+b1$ and below $S2(H/H0)=(a2-b2)*(1/(1+\exp(-c2((H/H0)-d2))))+b2$, where a1=100° C., a2=300° C., b1=300° C., b2=400° C., c1=50, c2=20, d1=0.2, and d2=0.8.

13. The method of claim 12, further comprising removing $AlCl_3$ from a product gas stream and analyzing the product gas stream by on-line gas chromatography or spectroscopy to obtain data on the composition of the product gas stream, and adjusting the temperature profile of the reactor from the data to optimize production of a desired chlorosilane product.

14. The method of claim 13, wherein $AlCl_3$ is removed from the gas stream by contacting solid sodium chloride forming a liquid adduct of sodium chloride and aluminum chloride, and collecting the liquid adduct in a collecting vessel below a container in which the solid sodium chloride is contained.

* * * * *

UNITED STATES PATENT AND TRADEMARK OFFICE
CERTIFICATE OF CORRECTION

PATENT NO. : 10,031,082 B2
APPLICATION NO. : 14/899147
DATED : July 24, 2018
INVENTOR(S) : Thorsten Goebel et al.

It is certified that error appears in the above-identified patent and that said Letters Patent is hereby corrected as shown below:

In the Claims

Column 10, Line 45, Claim 1:
After "a reactor height H0 in which"
Delete "HCI" and
Insert -- HCl --

Signed and Sealed this
First Day of January, 2019

Andrei Iancu
*Director of the United States Patent and Trademark Office*